United States Patent [19]

Holtkamp, Sr.

[11] Patent Number: Plant 7,133

[45] Date of Patent: Jan. 30, 1990

[54] AFRICAN VIOLET PLANT NAMED LITTLE CRYSTAL

[76] Inventor: Reinhold Holtkamp, Sr., Werther Strasse 112, D4294 Isselburg, Fed. Rep. of Germany

[21] Appl. No.: 310,758

[22] Filed: Feb. 15, 1989

[51] Int. Cl.[4] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Little Crystal which is a sport of Little Apatite, disclosed in U.S. Plant patent application Ser. No. 251,250. Little Crystal is characterized by its miniature growth habit; single, plain white flowers with elongated petals; strong stems which curve toward the center to form a compact bouquet above the leaves; profuse and continuous flowering; medium green, spear to heart-shaped leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionanatha*, and hereinafter referred to by the cultivar name Little Crystal.

The new cultivar was referred to during the breeding and selection process by the designation M/I 402 and is a sport of Little Apatite, disclosed in my U.S. Plant patent application Ser. No. 251,250. The female, or seed parent of Little Apatite was a cultivar designated 4 Mini. The male, or pollen parent of Little Apatite was a cultivar designated 69. Little Crystal is similar in all essential respect to Little Apatite except for its white color. Little Crystal was discovered in a flowering block of the parent cultivar Little Apatite, and subsequently selected. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Crystal has not been observed under all possible environmental conditions. The phenotype may vary significantly with variations in environment such as temperature, light intensity and day length. The following observations, measurements and values describe the new cultivar as grown in a 4 cm pot in Haffen, West Germany and Nashville, Tenn. under greenhouse conditions which closely approximate those generally used in commercial practice.

The following traits have been repeatedly observed and are determined to be basic characteristics of Little Crystal, which in combination distinguish this African violet as a new and distinct cultivar:

(1) Little Crystal is a miniature violet and will not grow taller than 6.8 cm.

(2) Single, (sometimes almost semi-double), white flowers with elongated petals.

(3) Strong wirelike and upright flower stems curving toward the center.

(4) First flash of flowers form a tight bouquet above the leaves.

(5) Profuse flowering; under good growing conditions continuous blooming.

(6) Each plant carries 7–10 and more upright flower stems each of which carries 4 and more flowers.

(7) Long lasting, non-dropping flowers.

(8) Plant saleable 10 to 11 weeks after planting of unrooted shoot.

(9) Seed capsules push slightly through.

(10) Medium green, hairy leaves.

(11) Spear to heart-shaped leaves are 2.0 to 2.5 cm in size.

(12) After maturity the flowers dry off and remain on the peduncle.

The accompanying color photographic drawing shows a typical specimen plant of the new cultivar grown in a 4 cm pot. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 1 p.m. in Nashville, Tenn.

Botanical Classification: *Saintpaulia ionantha*, Ramat., c.v. Little Crystal.

Parentage: Sport of Little Apatite disclosed in U.S. Plant patent application Ser. No. 251,250.

Propagation: The new cultivar holds its distinguishing characteristics through successive propagations by leaf cuttings.

Plant: From 4 cm to 6 cm tall when grown in pots, and approximately 8–10 cm in diameter when fully grown.

*Leaves.*—General form: Spear to heart-shaped. Diameter: 20–24 mm wide and 23–26 mm long. Texture: Leatherlike. Aspect: Shiny, hairy. Veins: Upperside: visible; underside: well pronounced, light green, shiny. Color (upperside): Green Group 137 A. Color (underside): Yellow-Green Group 147 D. Petiole: Strong, light green, hairy.

*Flowers.*—Buds: Size: 3–4 mm just before opening. Shape: Bell-shaped. Color: Light green. Sepals: Five (5). Color: Greenish brown. Calyx: Shape: Funnel-shaped. Aspect: Spear-shaped, hairy. Peduncle: Character: Strong, wirelike, upright, hairy. Color: Light green. Individual flowers:

Size: 21–24 mm. Shape: Single, (sometimes almost semi-double), violet-shaped, but with elongated petals, especially the 3 large ones. Color (upperside): Plain white. Color (underside): Plain white. Borne: Each flower stem carries 4 and more flowers on strong, upright peduncle that are free standing above the leaves, thereby forming a compact bouquet. Flowering habit: Flowers 10–11 weeks after planting an unrooted plantlet.

*Reproductive organs.*—Stamens: Two (2). Anthers: 2 composed of 4 anther cells, seed capsule pushed slightly through. Filaments: Greenish white, 2 mm long. Styles: 4–5 mm long, white, occasionally purplish red, base of ovary light green and hairy.

*Roots.*—Normally developed, white when young, turning slightly brownish when older.

Disease resistance: Good.

General observations: Little Crystal is a super miniature violet, which does not grow taller than 6–8 cm. The single, white flowers have elongated petals. Occasionally, 1–2 additional small petals develop in the center, sometimes even more, giving some flowers a semi-double look. The flowers are very long-lasting and non-dropping. Little Crystal has continuous blooming characteristics, and under good growing conditions, it will not stop blooming. A nice bouquet of flowers free standing above the leaves develops approximately 10–11 weeks after planting an unrooted plantlet. Each of the 7–10 and more strong flower stems carries 4 and more flowers. The medium green leaves are spear to heart-shaped.

I claim:

1. A new and distinct cultivar of African violet named Little Crystal, as described and illustrated, and particularly characterized by its miniature growth habit; single, plain white flowers with elongated petals; strong stems which curve toward the center to form a compact bouquet above the leaves; profuse and continuous flowering; medium green, spear to heart-shaped leaves; flowering 10–11 weeks after planting of unrooted shoot, and by its long lasting and non-dropping flowers.

* * * * *

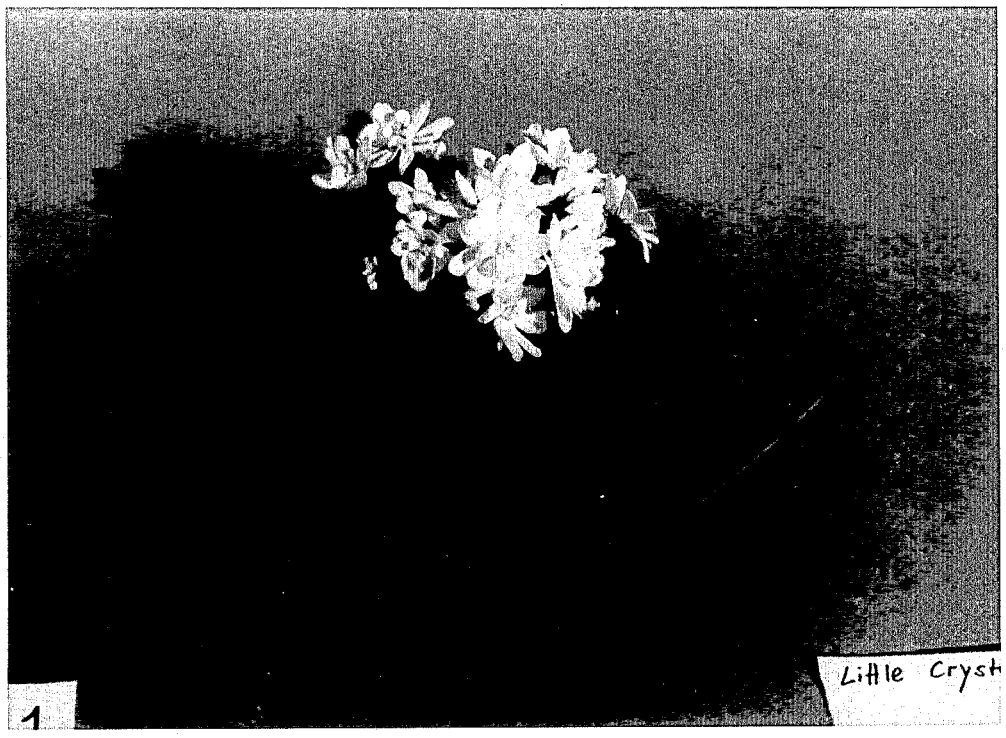
Little Cryst
1